(12) United States Patent
Ham et al.

(10) Patent No.: US 11,649,221 B2
(45) Date of Patent: May 16, 2023

(54) **METHOD OF ISOLATING TETRAHYDROCANNABINOL FROM *CANNABIS* PLANT AND USE THEREOF**

(71) Applicant: KOREA INSTITUTE OF SCIENCE AND TECHNOLOGY, Seoul (KR)

(72) Inventors: Jungyeob Ham, Gangneung-si (KR); Taejung Kim, Gangneung-si (KR); Bong Chul Chung, Seoul (KR); Sungdo Ha, Gangneung-si (KR); Seok Lee, Seoul (KR); Deok Ha Woo, Seoul (KR); Pilju Choi, Gangneung-si (KR); Bong Geun Song, Gangneung-si (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 354 days.

(21) Appl. No.: 16/916,920

(22) Filed: Jun. 30, 2020

(65) Prior Publication Data

US 2021/0002247 A1 Jan. 7, 2021

(30) Foreign Application Priority Data

Jul. 1, 2019 (KR) .................... 10-2019-0078957

(51) Int. Cl.
| | |
|---|---|
| *C07D 311/80* | (2006.01) |
| *A61K 8/49* | (2006.01) |
| *A61Q 19/00* | (2006.01) |
| *B01D 11/02* | (2006.01) |
| *A23L 33/105* | (2016.01) |

(52) U.S. Cl.
CPC .......... *C07D 311/80* (2013.01); *A23L 33/105* (2016.08); *A61K 8/498* (2013.01); *A61Q 19/00* (2013.01); *B01D 11/0211* (2013.01); *B01D 11/0288* (2013.01); *A23V 2002/00* (2013.01); *A61K 2800/10* (2013.01)

(58) Field of Classification Search
None
See application file for complete search history.

(56) References Cited

U.S. PATENT DOCUMENTS

2008/0221339 A1* 9/2008 Webster ............... C07D 311/80
549/390

FOREIGN PATENT DOCUMENTS

| CA | 3010636 A1 * | 1/2018 | .......... A61K 31/352 |
| WO | WO 2019/100172 A1 | 5/2019 | |

OTHER PUBLICATIONS

Gaoni et al, Tetrahedron, vol. 22, pp. 1481-1488, (Year: 1966).*
Chang et al., "Microwave-Assisted Extraction of Cannabinoids in Hemp Nut Using Response Surface Methodology: Optimization and Comparative Study," Molecules (2017), vol. 22, No. 1894, pp. 1-15.
Office Action dated Jan. 18, 2021, in Korean Patent Application No. 10-2019-0078957.
Pawar, H. et al., "Microwave assisted organocatalytic synthesis of 5-hydroxymethyl furfural in a monophasic green solvent sytem," RSC. Adv. (2014), vol. 4, pp. 26714-26720.
Andre et al., "Cannabis sativa: The Plant of the Thousand and One Molecules", Frontiers in Plant Science, Feb. 4, 2016, vol. 7, Article 19, pp. 1-17.
Burstein, "Cannabidiol (CBD) and its analogs: a review of their effects on inflammation", Bioorganic & Medicinal Chemistry, 2015, vol. 23, pp. 1377-1385.
Devane et al., "Isolation and Structure of a Brain Constituent That Binds to the Cannabinoid Receptor", Science, Dec. 18. 1992, vol. 258, pp. 1946-1949.
Russo et al., "Agonistic Properties of Cannabidiol at 5-HT1a Receptors", Neurochemical Research, Aug. 2005, vol. 30, No. 8, pp. 1037-1043.

* cited by examiner

*Primary Examiner* — Zinna Northington Davis
(74) *Attorney, Agent, or Firm* — Birch, Stewart, Kolasch & Birch, LLP

(57) ABSTRACT

Provided are a method of preparing a *cannabis* processed product having an increased Δ9-THC content in an efficient and economic manner, through a cyclization reaction by microwave irradiation of *cannabis* using various extraction solvents, and use of the processed product having an increased Δ9-THC content prepared by the method, a fraction thereof, and a single ingredient of THC, in foods, drugs, and cosmetics.

11 Claims, 10 Drawing Sheets

| Peak# | Ret. Time | Area | Height | Mark | Conc. | Unit | ID# | Name | Area% |
|---|---|---|---|---|---|---|---|---|---|
| 1 | 16.932 | 24406 | 4028 | M | 0.870 | | | | 0.870 |
| 2 | 18.708 | 5650 | 1039 | M | 0.201 | | | | 0.201 |
| 3 | 19.360 | 2674195 | 447968 | M | 95.276 | | | | 95.276 |
| 4 | 19.640 | 13314 | 2253 | M | 0.474 | | | | 0.474 |
| 5 | 20.052 | 27909 | 4934 | M | 0.994 | | | | 0.994 |
| 6 | 21.479 | 41828 | 5932 | M | 1.490 | | | | 1.490 |
| 7 | 22.425 | 19494 | 2591 | | 0.695 | | | | 0.695 |
| Total | | 2806795 | 468744 | | 100.000 | | | | 100.000 |

METHOD OF ISOLATING TETRAHYDROCANNABINOL FROM *CANNABIS* PLANT AND USE THEREOF

CROSS-REFERENCE TO RELATED APPLICATION

This application claims the benefit of Korean Patent Application No. 10-2019-0078957, filed on Jul. 1, 2019, in the Korean Intellectual Property Office, the disclosure of which is incorporated herein in its entirety by reference.

BACKGROUND

1. Field

The present disclosure relates to a method of isolating tetrahydrocannabinol (THC) from a *cannabis* plant using microwave, and use thereof.

2. Description of Related Art

*Cannabis* (*Cannabis sativa* L.) is an annual plant belonging to the genus *Cannabis* in the family Cannabaceae, which has been widely cultivated in temperate and tropical areas, mainly in Central Asia for 12,000 years, and includes wild-type *cannabis*, and it collectively refers to *cannabis* chemovars, which contain different kinds of cannabinoid compounds known as medical/pharmaceutical ingredients, and variants thereof, *Cannabis sativa* subspecies *sativa* including variants var. *indica* and var. *kafiristanica*, *Cannabis sativa* subspecies *indica*, *Cannabis sativa* subspecies *ruderalis*, and also plants which are the result of genetic crosses, self-crosses, or hybrids thereof.

According to Korean and Chinese traditional medical records, mazain (麻子仁) or hwamain (火麻仁), which is a peeled seed of *cannabis*, has been used for constipation, diabetes, pain diseases, menstrual disorders, skin diseases, dysentery, etc., and *cannabis* weed which is a *cannabis* leaf has been used for anthelmintic, hair protection, asthma, analgesic, anesthetic, diuretic purposes, etc. Further, *cannabis* root has been used to treat difficult deliveries and to relieve blood stasis, *cannabis* skin has been used for bruises, and irritant rash and distending pain, *cannabis* flower has been used for paralysis, itching, etc., and *cannabis* flower neck has been used for difficult deliveries, constipation, gout, insanity, insomnia, etc. There are records that all parts of *cannabis* are appropriately used according to diseases.

*Cannabis* includes about 400 compounds, and most of them are cannabinoids, terpenes, and phenolic compounds. There are about 90 kinds of cannabinoids, which are medically/pharmacologically important natural ingredients, and there are many ingredients found only in *cannabis* (*Frontiers in Plant Science* 2016, 7, 19).

Among the ingredients of *cannabis*, substances known as psychotropic cannabinoids are Δ9-tetrahydrocannabinol (Δ9-THC), cannabinol (CBN), cannabinodiol (CBDL), and cannabidiol (CBD), which is a non-psychotropic ingredient, is known to exhibit physiologically active effects through various receptors in the human body, including adrenergic receptors and cannabinoid receptors.

In particular, while scientists were studying the mechanism of psychotropic action of *cannabis*, they discovered in 1988 a receptor in the brain, to which cannabinoid selectively binds, indicating that molecules similar to cannabinoid are also produced in our body. These cannabinoid molecules are fatty acid-type neurotransmitters locally produced in the brain, and also called anandamide (*Science*, 1992, 258, 1946). *Cannabis* receptors currently known are divided into two kinds; CB1 receptors are distributed throughout the brain, such as the cerebral cortex, hippocampus, cerebellum, basal ganglia, etc., and CB2 receptors are mainly distributed in macrophages or peripheral tissues such as bone marrow, lungs, pancreas, smooth muscles, etc., and are closely related to the immune system.

THC, which is a main active ingredient of *cannabis* used for medicinal purposes, is an agonist with a strong affinity for CB1 receptor, and exhibits a main mechanism of psychotropic action, whereas many experimental results revealed that CBD has beneficial effects such as anti-inflammatory action, antiepileptic action, antiemetic action, anti-cancer action, etc. CBD reduces negative effects of THC (*Bioorganic Medicinal Chemistry*, 2015, 23, 1377), and inhibits reuptake and breakdown of anandamide which is an endogenous cannabinoid, through antagonistic action on CB1 and CB2 receptor agonists such as THC, and is also known as a serotonin receptor agonist (*Neurochemcal Research*, 2005, 30, 1037). It was also revealed that cannabichromene which is an ingredient of *cannabis* has anti-inflammatory, sedative, antifungal actions, etc., and CBN helps boost immune function by binding to CB2 receptor rather than CB1 receptor (*Frontiers in Plant Science* 2016, 7, 19), and many researches have been very actively conducted on pharmacological mechanisms of ingredients included in *cannabis*.

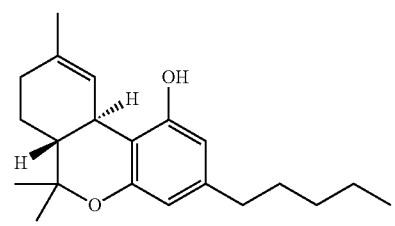

Δ9-Tetrahydrocannabinol, Δ9-THC

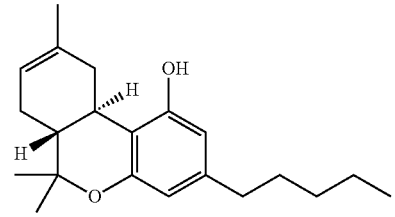

Δ8-Tetrahydrocannabinol, Δ8-THC

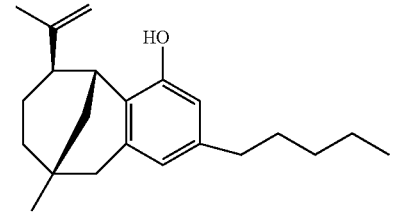

Δ8-iso-Tetrahydrocannabinol, Δ8-iso-THC

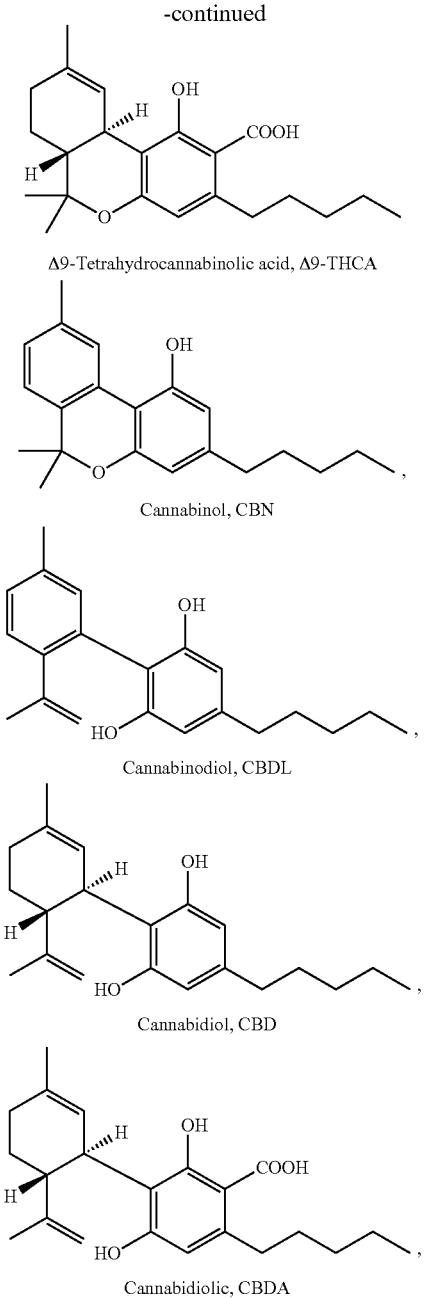

Δ9-Tetrahydrocannabinolic acid, Δ9-THCA

Cannabinol, CBN

Cannabinodiol, CBDL

Cannabidiol, CBD

Cannabidiolic, CBDA

Dronabinol (brand name: Marinol) and nabilone (brand name: Cesamet), which are THC oral forms approved by the US Food and Drug Administration (FDA), are being sold as relievers for chemotherapy-induced side-effects and as appetite stimulants for AIDS patients (*Journal of Nurse Practitioners* 2014, 10, 633), and extensive studies have been actively conducted, such as clinical trials for Epidiolex which is a liquid drug including CBD as a main ingredient for children with epilepsy, Resunab which is a CB2 receptor-binding synthetic cannabinoid formulation in the treatment of systemic lupus erythematosus, Cannador (THC:CBD=2:1) which is not a single THC or CBD drug but in the form of a *cannabis* extract in the treatment of multiple sclerosis and severe chronic pain disorders, etc.

Accordingly, the present inventors have developed technologies to increase extraction yields of the main pharmaceutical ingredients of *cannabis* and to increase a content of THC using a microwave processing technology which has been accumulated until now, and as a result, they found that Δ9-THC is easily converted from CBDA and CBD through a microwave decarboxylic acid reaction and a cyclization reaction using an oil-soluble organic solvent, thereby completing the present disclosure.

SUMMARY

An aspect provides a method of isolating Δ9-tetrahydrocannabinol (THC) from a *cannabis* plant, the method including irradiating microwaves to a reaction mixture including a cannabidiol (CBD)-containing sample, a Lewis acid, and a solvent in an airtight container.

Another aspect provides a composition including Δ9-THC isolated by the above method.

Additional aspects will be set forth in part in the description which follows and, in part, will be apparent from the description, or may be learned by practice of the presented embodiments of the disclosure.

An aspect provides a method of isolating Δ9-tetrahydrocannabinol (THC) from a *cannabis* plant, the method including irradiating microwaves to a reaction mixture including a cannabidiol (CBD)-containing sample, a Lewis acid, and a solvent in an airtight container.

In the method, the CBD-containing sample may include any sample, as long as it contains CBD. The CBD-containing sample may be a *Cannabis* sp. plant or an extract thereof, or a CBD compound itself. The *Cannabis* sp. plant may include *Cannabis* sp., such as *Cannabis chemovars, Cannabis sativa, Cannabis indica, Cannabis ruderalis*, etc., wild sp. thereof, variants thereof, mutants thereof, hybrids thereof, and plants including cannabinoid, etc. Further, the *Cannabis* sp. plant may be a living plant or a dried plant. Further, the *Cannabis* sp. plant may be leaves, flower buds, fruits, trichomes, flower bracts, stems, or any part including cannabinoid. Further, the *Cannabis* sp. plant may be a dioecious plant, and its cannabinoid content may vary depending on female and male plants. The *Cannabis* sp. plant may be a female plant, a male plant, or a mixture thereof.

In the method, the Lewis acid may be an organic acid or an inorganic acid. The Lewis acid may be a sulfonic acid. The sulfonic acid may be, for example, an acid having a structure of Formula I.

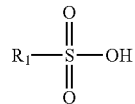

(Formula I)

In Formula I, R1 is a C5-C12 aryl group, a C1-C12 alkyl group, a C3-C12 cycloalkyl group, a C3-C12 cycloketone group, or a C6-C12 arylalkyl group, and the aryl, alkyl, cycloalkyl, cycloketone, or arylalkyl group may have one or more substituents selected from the group consisting of halogen and a C1-C6 alkyl group. In a specific embodiment, R1 is a C6-C12 aryl group, a C1-C6 alkyl group, a C6-C12 cycloalkyl group, a C6-C12 cycloketone group, or a C6-C10 arylalkyl group, and the aryl, alkyl, cycloalkyl, cycloketone, or arylalkyl group may have one or more substituents selected from the group consisting of halogen and a C1-C6 alkyl group. In a specific embodiment, R1 may be a phenyl group, a benzyl group, a tolyl group, a biphenyl group, a naphthyl group, a C1-C8 alkyl group, a C6-C12 cycloalkyl group, or a C7-C12 arylalkyl group. The sulfonic acid is, for example, methanesulfonic acid (MSA), benzenesulfonic acid, naphthalenesulfonic acid, toluenesulfonic acid containing para-toluenesulfonic acid (p-toluensulfonic acid, PTSA), or camphor-10-sulfonic acid (CSA). The Lewis acid may also be formic acid, acetic acid, propionic acid, lactic acid, citric acid, tartaric acid, succinic acid, fumaric acid, maleic acid, malonic acid, mandelic acid, malic acid, phthalic acid, hydrochloric acid, sulfuric acid, or nitric acid.

The term "alkyl" refers to a straight or branched saturated hydrocarbon group. The alkyl is, for example, methyl, ethyl, n-propyl, isopropyl, n-butyl, isobutyl, t-butyl, n-pentyl, isopentyl, neopentyl, n-hexyl, n-heptyl, n-octyl, n-nonyl or n-decyl.

The term "aryl" refers to an aromatic ring in which each atom forming a ring is a carbon atom. The ring may be a monocyclic or polycyclic ring. The polycyclic ring may include those having a fused ring (e.g., naphthalene) or a non-fused ring (e.g., biphenyl). The polycyclic ring may have, for example, 2 rings, 3 rings, or 4 rings. The aryl group has, for example, 5 or more, 6 or more, 7 or more, 8 or more, 9 or more, 10 or more, 5 to 12, 5 to 10, or 6 to 10 carbon ring atoms. The aryl group includes, for example, phenyl, naphthalenyl (e.g., naphthalen-1-yl and naphthalen-2-yl), and biphenyl.

The term "cycloalkyl" refers to a non-aromatic carbon ring in which each atom forming a ring is a carbon atom. The cycloalkyl may be monocyclic or polycyclic. The polycyclic may be, for example, those having 2, 3, or 4 fused rings. The cycloalkyl may include those fused to an aromatic ring. The cycloalkyl includes, for example, 3 or more, 4 or more, 5 or more, 6 or more, 7 or more, 3 to 10, 3 to 7, 5 to 7, or 5 to 6 ring carbon atoms. The cycloalkyl includes cyclopropyl, cyclobutyl, cyclopentyl, cyclohexyl, cycloheptyl, cyclohexadienyl, cycloheptatrienyl, norbornyl, norcanyl, and adamantyl.

The term "cycloketone" refers to "cycloalkyl" having a ketone group.

The term "arylalkyl" refers to alkyl substituted with aryl.

The term "halogen" refers to fluoro, chloro, bromo, or iodo.

In the method, a concentration of the Lewis acid may be 0.004 M to 0.12 M. The concentration of the Lewis acid may be, for example, 0.02 M to 0.12 M, 0.04 M to 0.12 M, 0.08 M to 0.12 M, 0.02 M to 0.08 M, or 0.04 M to 0.08 M.

In the method, the solvent is not particularly limited. The solvent may be, for example, a protonic polar solvent, or an aprotic polar or non-polar solvent. The protonic polar solvent may be water, methanol, ethanol, propanol, isopropanol, or butanol. The aprotic polar solvent may be dichloromethane, tetrahydrofuran, ethyl acetate, acetonitrile, dimethylformamide, dimethyl sulfoxide, acetone, 2-butanone, or hexamethylphosphoramide. The non-polar solvent may be pentane, hexane, chloroform, or diethyl ether. The non-polar solvent excludes benzene. The solvent may be C1-C6 alcohol, C3-C10 ester, for example, C3-C10 acetate, C3-C10 ketone, C1-C6 unsubstituted or halogenated hydrocarbon, C2-C10 cyclic ether, a mixture thereof, or a mixture of one or more of the solvents and water. The solvent may be ethanol, propanol, acetonitrile, ethyl acetate, acetone, 2-butanone, chloroform, dichloromethane, hexane, a mixture thereof, or a mixture of one or more of the solvents and water. The hydrocarbon may be alkane, alkene, or alkyne.

In the method, the microwave irradiation may be carried out at 50° C. to 90° C. The microwave irradiation may be carried out at, for example, 50° C. to 80° C., 50° C. to 70° C., 50° C. to 60° C., 60° C. to 90° C., 60° C. to 80° C., 60° C. to 70° C., 70° C. to 90° C., 70° C. to 80° C., or 80° C. to 90° C.

In the method, the microwave irradiation may be carried out at 1 atm to 15 atm. The microwave irradiation may be carried out at, for example, 2 atm to 15 atm, 5 atm to 15 atm, 7 atm to 15 atm, 10 atm to 15 atm, 1 atm to 10 atm, 1 atm to 5 atm, 1 atm to 3 atm, or 2 atm to 10 atm.

In the method, the microwave irradiation may be carried out for a time sufficient to convert CBD to THC by cyclization. The microwave irradiation may be carried out for a time sufficient to convert CBD to Δ9-THC with higher selectivity than Δ8-THC, by cyclization. The microwave irradiation may be carried out for 10 min to 90 min. The microwave irradiation may be carried out for, for example, 10 min to 80 min, 10 min to 70 min, 10 min to 60 min, 10 min to 50 min, 10 min to 40 min, 10 min to 30 min, 10 min to 20 min, 20 min to 90 min, 20 min to 60 min, 20 min to 50 min, 20 min to 40 min, 20 min to 30 min, 30 min to 90 min, 30 min to 60 min, 30 min to 50 min, 30 min to 40 min, 40 min to 90 min, 40 min to 60 min, 40 min to 50 min, 50 min to 90 min, 40 min to 60 min, or 60 min to 90 min.

In the method, the Lewis acid may be para-toluene sulfonic acid, and the solvent may be ethyl acetate.

In the method, the CBD-containing sample may be obtained by a method including irradiating microwaves to a mixture including *cannabis* leaves or a solvent extract thereof and a solvent in an airtight container.

In the method, the solvent extract may be obtained by a method including incubating a reaction mixture including *cannabis* leaves and a solvent.

In the method, the solvent is not particularly limited. The solvent may be, for example, a protonic polar solvent, or an aprotic polar or non-polar solvent. The protonic polar solvent may be water, methanol, ethanol, propanol, isopropanol, or butanol. The aprotic polar solvent may be dichloromethane, tetrahydrofuran, ethyl acetate, acetonitrile, dimethylformamide, dimethyl sulfoxide, acetone, 2-butanone, or hexamethylphosphoramide. The non-polar solvent may be pentane, hexane, chloroform, or diethyl ether. The non-polar solvent excludes benzene.

The solvent may be C1-C6 alcohol, C3-C10 ester, for example, C3-C10 acetate, C3-C10 ketone, C1-C6 unsubstituted or halogenated hydrocarbon, C2-C10 cyclic ether, a mixture thereof, or a mixture of one or more of the solvents and water. The solvent may be ethanol, propanol, acetonitrile, ethyl acetate, acetone, 2-butanone, chloroform, dichloromethane, hexane, a mixture thereof, or a mixture of one or more of the solvents and water. The hydrocarbon may be alkane, alkene, or alkyne.

In the method, the incubating may be carried out under microwave irradiation. The microwave irradiation may be carried out using an ultrasonic processor at 40% power of the instrument for 1 hr.

In the method, the microwave irradiation may be carried out at 50° C. to 120° C. The microwave irradiation may be carried out at, for example, 50° C. to 90° C., 50° C. to 80° C., 80° C. to 120° C., 80° C. to 90° C., or 90° C. to 120° C.

In the method, the microwave irradiation may be carried out at 1 atm to 15 atm. The microwave irradiation may be carried out at, for example, 2 atm to 15 atm, 5 atm to 15 atm, 7 atm to 15 atm, 10 atm to 15 atm, 1 atm to 10 atm, 1 atm to 5 atm, 1 atm to 3 atm, or 2 atm to 10 atm.

In the method, the microwave irradiation may include converting CBDA to CBD by decarboxylation. The microwave irradiation may be carried out at 80° C. to 130° C., for example, 100° C. to 130° C., or 80° C. to 110° C. for 10 min to 90 min, for example, 20 min to 90 min, 10 min to 60 min, 20 min to 60 min, 30 min to 90 min, 30 min to 60 min, or 30 min.

In the method, the microwave irradiation may be carried out for a time sufficient to convert CBDA to CBD by decarboxylation. The microwave irradiation may be carried out for 10 min to 90 min. The microwave irradiation may be carried out for, for example, 10 min to 80 min, 10 min to 70 min, 10 min to 60 min, 10 min to 50 min, 10 min to 40 min, 10 min to 30 min, 10 min to 20 min, 20 min to 80 min, 20 min to 70 min, 20 min to 60 min, 20 min to 50 min, 20 min to 40 min, 20 min to 30 min, 30 min to 80 min, 30 min to 70 min, 30 min to 60 min, 30 min to 50 min, or 30 min to 40 min.

In the method, the solvent extract, which is a product obtained by incubating, may not undergo additional isolation. The method may further include isolating CBD from the solvent extract, which is a product obtained by incubating. The isolating CBD may be, for example, removing the solvent. In the method, the solvent may be ethyl acetate.

In the method, the product obtained by microwave irradiation may have higher selectivity for Δ9-THC than selectivity for Δ8-THC or Δ8-iso-THC.

In the method, the product obtained by microwave irradiation may have a ratio of Δ9-THC to Δ8-THC at 1.0:1.6 to 3.5, based on the weight.

The method may further include isolating THC from the reaction product obtained by microwave irradiation. The isolating THC may include distillation, crystallization, chromatography, or filtration.

Another aspect provides a composition including THC isolated by the above method. The composition may include THC of 0.01% to 30%, for example, 0.01% to 20%, 0.01% to 15%, 0.01% to 10%, 0.1% to 30%, 0.1% to 20%, 0.1% to 15%, 0.1% to 10%, 0.1% to 5.3%, 0.5 to 5.3%, 1.0% to 5.3%, 0.1% to 5%, 0.1% to 3%, 0.5% to 5%, or 1.0% to 5%, based on the total weight of the composition. In the composition, a content of Δ9-THC is 150% to 340%, as compared with a content of Δ8-THC, based on the weight.

Still another aspect provides an antiepileptic, neuroprotective, vasorelaxant, anti-cancer, anti-inflammatory, anti-diabetic, anti-bacterial, analgesic, anti-osteoporosis, immune-enhancing, or antiemetic pharmaceutical composition, the pharmaceutical composition including, as an active ingredient, THC isolated by the above method. The THC may be in the form of an extract, a fraction, or a single ingredient. The pharmaceutical composition may further include a pharmaceutically acceptable carrier or diluent.

The THC has improved THC efficacy due to a significantly high content of THC, as compared with a processed product resulting from simple heat-treatment. THC is known to have antiepileptic, neuroprotective, vasorelaxant, anti-cancer, anti-inflammatory, anti-diabetic, anti-bacterial, analgesic, anti-osteoporosis, immune-enhancing, or antiemetic effects. Therefore, these effects may be significantly increased by the microwave irradiation, as compared with a processed product resulting from simple heat-treatment.

Still another aspect provides a health functional food composition including, as an active ingredient, THC isolated by the above method. The THC may be in the form of an extract, a fraction, or a single ingredient. The food may be a functional food or a health functional food. The functional ingredient of the food is a safe food composition partially including the pharmaceutical ingredient, and may further include a carrier or diluent acceptable for use in foods.

Still another aspect provides a cosmetic composition including, as an active ingredient, THC isolated by the above method. The cosmetics may be a general cosmetics or a functional cosmetics. THC, known as a functional ingredient of cosmetics, may be a composition having an antioxidant or anti-inflammatory effect. The cosmetic composition may further include a carrier or diluent acceptable for use in cosmetics.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
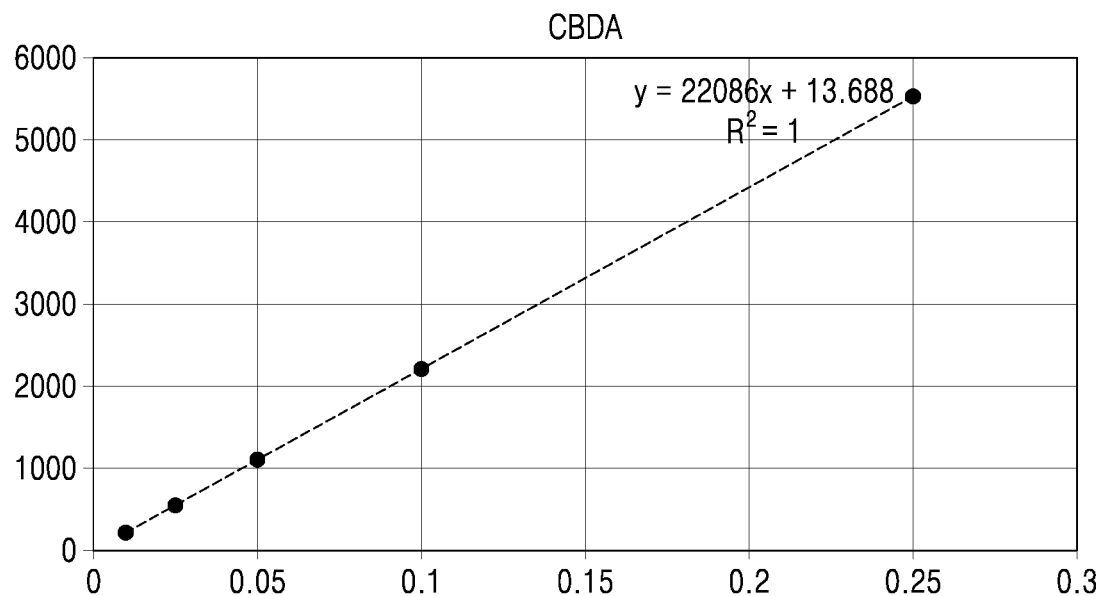
FIG. 1 shows a calibration curve constructed by analyzing CBDA according to concentrations.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, the present disclosure will be described in more detail with reference to exemplary embodiments. However, these exemplary embodiments are only for illustrating the present disclosure, and the scope of the present disclosure is not limited to these exemplary embodiments.

Example 1: Preparation of *Cannabis* Extract

*Cannabis* used in the present Examples was deposited by JayHempKorea Ltd., located in Sangju city, Gyeongsangbuk-do, South Korea, through assignment/transfer approval processes under drug (*cannabis*) research permission (No. 1564) obtained from the Ministry of Food and Drug Safety and Seoul Regional Food and Drug Administration.

*Cannabis* seed skins, *cannabis* leaves, *cannabis* stems, and *cannabis* roots were harvested in October, 2018, and used after being dried and finely cut. 2 L of ethyl acetate which is an extraction solvent was added to 200 g of finely cut and dried *cannabis* leaves having a relatively high content of cannabinoids among the parts of *cannabis* in a 5 L beaker, and extracted using an ultrasonic processor (Sonics, VC505) at 40% power of the instrument for 1 hr, and then extraction was repeated twice at room temperature for 24 hr. The liquid extract was concentrated by evaporation under reduced pressure to obtain 17.6 g of a dry extract containing CBDA and CBD.

Example 2: Microwave Processing of *Cannabis* Leaf Extract

The ethyl acetate extract obtained in Example 1 was subjected to microwave processing. In detail, 100 mg of the *cannabis* leaf extract was added to 1 mL of ethyl acetate in a 10-mL container of a microwave irradiator (model no. 908005) manufactured by CEM Company (USA), followed by sealing the container. Microwaves were irradiated at 120° C. and 100 W and a frequency of 2450 MHz for 30 min (Example 2). The product was dried under reduced pressure to obtain a microwave-irradiated processed product. A pressure for the microwave irradiation was 1 atm to 15 atm. Content analysis was performed according to an analysis method of Experimental Example 1.

Examples 3 to 11: Acid Addition Microwave Processing

Microwave processing was performed by adding acetic acid, citric acid, formic acid, hydrochloric acid, sulfuric acid, nitric acid, para-toluenesulfonic acid (PTSA), methanesulfonic acid (MSA), or camphor-10-sulfonic acid (CSA) to the microwave-irradiated processed product obtained in Example 2. In detail, 1 mL of ethyl acetate was added to 100 mg of the processed product obtained in Example 2 in a 10-mL container of a microwave irradiator (model no. 908005) manufactured by CEM Company (USA), and then acetic acid, citric acid, formic acid, hydrochloric acid, sulfuric acid, nitric acid, PTSA, MSA, or CSA was added thereto at a concentration of 0.08 M, followed by sealing the container. Processing was carried out at 80° C. and 100 W and a frequency of 2450 MHz for 20 min. According to the used acid, microwave processing was carried out by adding acetic acid (Example 3), citric acid (Example 4), formic acid (Example 5), hydrochloric acid (Example 6), sulfuric acid (Example 7), nitric acid (Example 8), PTSA (Example 9), MSA (Example 10), and CSA (Example 11). A pressure for the microwave irradiation was 1 atm to 15 atm. Contents thereof were analyzed according to an analysis method of Experimental Example 1.

Examples 12 to 21: Microwave Processing According to Solvents after Addition of Para-Toluenesulfonic Acid PTSA was added to the microwave-processed product obtained in Example 2, and microwave processing was carried out in ethanol, propanol, butanol, acetonitrile, ethyl acetate, acetone, 2-butanone, chloroform, dichloromethane, or hexane. In detail, 1 mL of ethanol (Example 12), propanol (Example 13), butanol (Example 14), acetonitrile (Example 15), ethyl acetate (Example 16), acetone (Example 17), 2-butanone (Example 18), chloroform (Example 19), dichloromethane (Example 20), or hexane (Example 21) was added to 100 mg of the processed product obtained in Example 2 in a 10-mL container of a microwave irradiator (model no. 908005) manufactured by CEM Company (USA), followed by sealing the container. Microwave irradiation was carried out at 80° C. and 100 W and a frequency of 2450 MHz for 20 min. A pressure for the microwave irradiation was 1 atm to 15 atm. Content analysis was performed according to an analysis method of Experimental Example 1.

Examples 22 to 39: Microwave Processing According to Temperature and Time after Addition of Para-Toluenesulfonic Acid Ethyl acetate was added to the microwave-processed product obtained in Example 2, and PTSA at various concentrations was added thereto, followed by microwave processing. In detail, 1 mL of ethyl acetate was added to 100 mg of the processed product obtained in Example 2 in a 10-mL container of a microwave irradiator (model no. 908005) manufactured by CEM Company (USA), and PTSA was added at a concentration of 0.004 M, 0.02 M, 0.04 M, or 0.08 M, followed by sealing the container. Microwave irradiation was carried out at 100 W and a frequency of 2450 MHz, respectively. Microwave irradiation was carried out at a PTSA concentration of 0.004 M and a temperature of 80° C. for 30 min (Example 22), at a PTSA concentration of 0.02 M and a temperature of 80° C. for 30 min (Example 23), at a PTSA concentration of 0.04 M and a temperature of 80° C. for 30 min (Example 24), for 60 min (Example 25), and for 90 min (Example 26), at a PTSA concentration of 0.08 M and a temperature of 80° C. for 10 min (Example 27), for 20 min (Example 28), for 30 min (Example 29), and for 40 min (Example 30), at a PTSA concentration of 0.12 M and a temperature of 80° C. for 10 min (Example 31), for 20 min (Example 32), and for 30 min (Example 33), at a PTSA concentration of 0.08 M and a temperature of 50° C. for 30 min (Example 34), for 60 min (Example 35), and for 90 min (Example 36), at a PTSA concentration of 0.08 M and a temperature of 90° C. for 10 min (Example 37), for 20 min (Example 38), and for 30 min (Example 39), respectively. A pressure for the microwave irradiation was 1 atm to 15 atm. Content analysis was performed according to an analysis method of Experimental Example 1.

Examples 40 to 44: Microwave Processing after Addition of Para-Toluenesulfonic Acid to *Cannabis* Leaf Extract Ethyl acetate and para-toluenesulfonic acid were added to the *cannabis* leaf extract obtained in Example 1, followed by microwave processing. In detail, 1 mL of ethyl acetate was added to 100 mg of the extract obtained in Example 1 in a 10-mL container of a microwave irradiator (model no. 908005) manufactured by CEM Company (USA), and para-toluenesulfonic acid was added at a concentration of 0.08 M, followed by sealing the container. Microwave irradiation was carried out at 80° C. and 100 W and a frequency of 2450 MHz, respectively. Microwave irradiation was carried out for a processing time of 10 min (Example 40), 20 min (Example 41), 30 min (Example 42), 40 min (Example 43), and 50 min (Example 44), respectively. A pressure for the microwave irradiation was 1 atm to 15 atm. Content analysis was performed according to an analysis method of Experimental Example 1.

Examples 45 to 51: General Heat Processing after Addition of Para-Toluenesulfonic Acid PTSA was added to the microwave processed product obtained in Example 2, followed by heat processing in the presence of ethyl acetate in an oil bath. In other words, to compare with a general heating experiment of using no microwave, heating was performed in a bath using oil as a medium. In detail, 1 mL of ethyl acetate was added to 100 mg of the processed product obtained in Example 2 in a 10-mL microwave container, and PTSA was added at a concentration of 0.08 M, followed by sealing the container. Heat processing was carried out in the oil bath set to a temperature of 80° C. for 30 min (Example 45), 60 min (Example 46), 90 min (Example 47), 120 min (Example 48), 180 min (Example 49), 240 min (Example 50), and 360 min (Example 51), respectively. Content analysis was performed according to an analysis method of Experimental Example 1.

Example 52 to 63: Microwave Processing of *Cannabis* Leaves

The finely cut and dried *cannabis* leaves were subjected to microwave processing. In detail, 7 mL of ethyl acetate was added to 1 g of *cannabis* leaves in a 40-mL container of a microwave irradiator (model no. 908005) manufactured by CEM Company (USA), followed by sealing the container. Primary processing was carried out at 130° C. and 300 W and a frequency of 2450 MHz for 30 min (Example 52). After primary processing, PTSA was added to the primary processed product at a concentration of 0.08 M, and microwave irradiation was carried out at 80° C. and 300 W and a frequency of 2450 MHz for 20 min (Example 53), 30 min (Example 54), and 40 min (Example 55), respectively. Further, 7 mL of ethanol was added to 1 g of dry *cannabis* in a 40-mL container, followed by sealing the container. Processing was carried out at 130° C. and 300 W and a frequency of 2450 MHz for 30 min, and then PTSA was added at a concentration of 0.08 M, and microwave irradiation was carried out at 80° C. and 300 W and a frequency of 2450 MHz for 20 min (Example 56), 30 min (Example 57), 40 min (Example 58), and 50 min (Example 59), respectively. Further, 7 mL of propanol was added to 1 g of dry *cannabis* in a 40-mL container, followed by sealing the container. Processing was carried out at 130° C. and 300 W and a frequency of 2450 MHz for 30 min, and then PTSA was added at a concentration of 0.08 M, and microwave irradiation was carried out at 80° C. and 300 W and a frequency of 2450 MHz for 20 min (Example 60), 30 min (Example 61), 40 min (Example 62), and 50 min (Example 63), respectively. A pressure for the microwave irradiation was 1 atm to 15 atm. Content analysis was performed according to an analysis method of Experimental Example 1. The primary processed product was continuously subjected to secondary processing without a separation process.

Example 64: Microwave Processing after Addition of Para-Toluenesulfonic Acid in Presence of Benzene Solvent Benzene was added to the microwave-processed product obtained in Example 2, and para-toluenesulfonic acid was added thereto, followed by microwave processing. In detail, 1 mL of benzene was added to 100 mg of the processed product obtained in Example 2 in a 10-mL container of a microwave irradiator (model no. 908005) manufactured by CEM Company (USA), and para-toluenesulfonic acid was added at a concentration of 0.08 M, followed by sealing the container. Microwave irradiation was carried out at 100 W, a frequency of 2450 MHz, and a temperature of 80° C. for 10 min (Example 64). A pressure for the microwave irradiation was 1 atm to 5 atm. Content analysis was performed according to an analysis method of Experimental Example 2, and compared with Example 28.

Experimental Example 1: Cannabinoid Analysis of Extract and Microwave-Processed Product (1) Experimental Method Based on values of CBDA, CBD, and Δ9-THC calibration curves, cannabinoids in the *cannabis* extracts and the processed extracts obtained in Comparative Examples and Examples were analyzed, and repeated in triplicate to confirm reproducibility. As for CBDA, CBD, and Δ9-THC single ingredients used in the experiments, purity of 97.1% (CBDA), purity of 96.3% (CBD), and purity of 96.8% (Δ9-THC) directly isolated from the *cannabis* raw material were used. According to the general calibration curve analysis method, CBDA, CBD, and Δ9-THC were prepared at 10 ppm, 25 ppm, 50 ppm, 100 ppm, and 250 ppm, respectively, and calibration curves were constructed. An elution solvent A and an elution solvent B used in ultra-performance liquid chromatography (UPLC) were water and acetonitrile, respectively, and each was pumped using two pumps. 3 μl of the standard aqueous solution was injected into a reverse-phase column for analysis (Phenomenex Luna Omega 1.6μ Polar C18, 150 mm×2.1 mm) using a syringe, and an elution solvent consisting of 70% by volume of A and 30% by volume of B was applied at a flow rate of 0.3 mL/min. Thereafter, % volume of the elution solvent B were gradually changed to 100% (20 min), 100% (23 min), and 30% (26 min). After the above procedures, each ingredient isolated from the column was analyzed by UV spectrum.

(2) Experimental Results

As a result of the experiments, each ingredient isolated from the column was analyzed through UPLC chromatogram by UPLC analysis of the *cannabis* extracts, and results of FIGS. 1 to 12 were obtained.

FIG. 1 shows a calibration curve constructed by analyzing CBDA according to concentrations.

Figure 2:
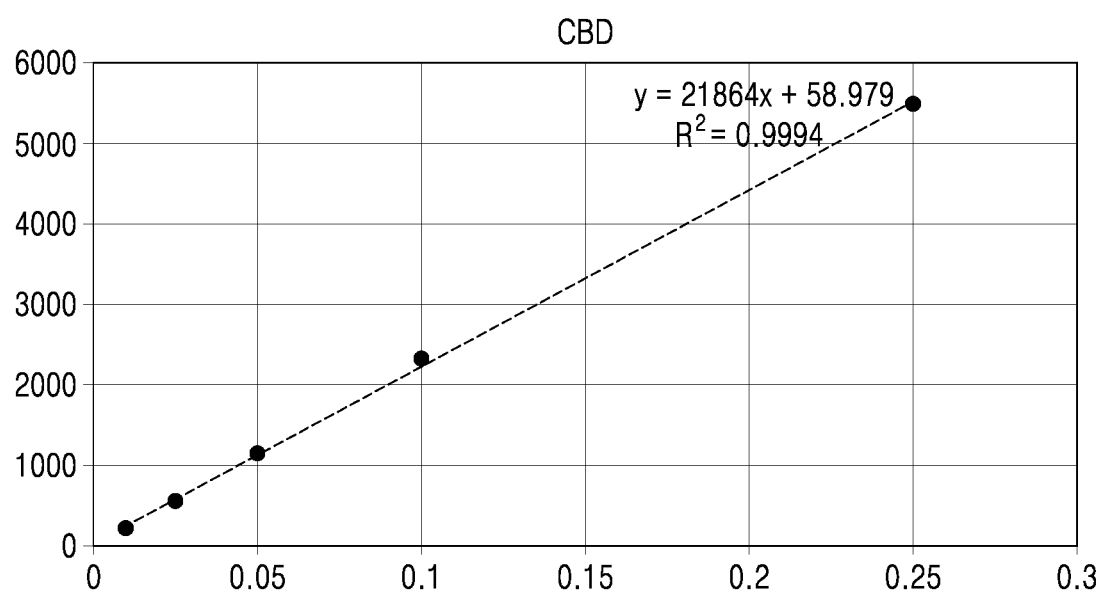
FIG. 2 shows a calibration curve constructed by analyzing CBD according to concentrations.

FIG. 2 shows a calibration curve constructed by analyzing CBD according to concentrations.

Figure 3:
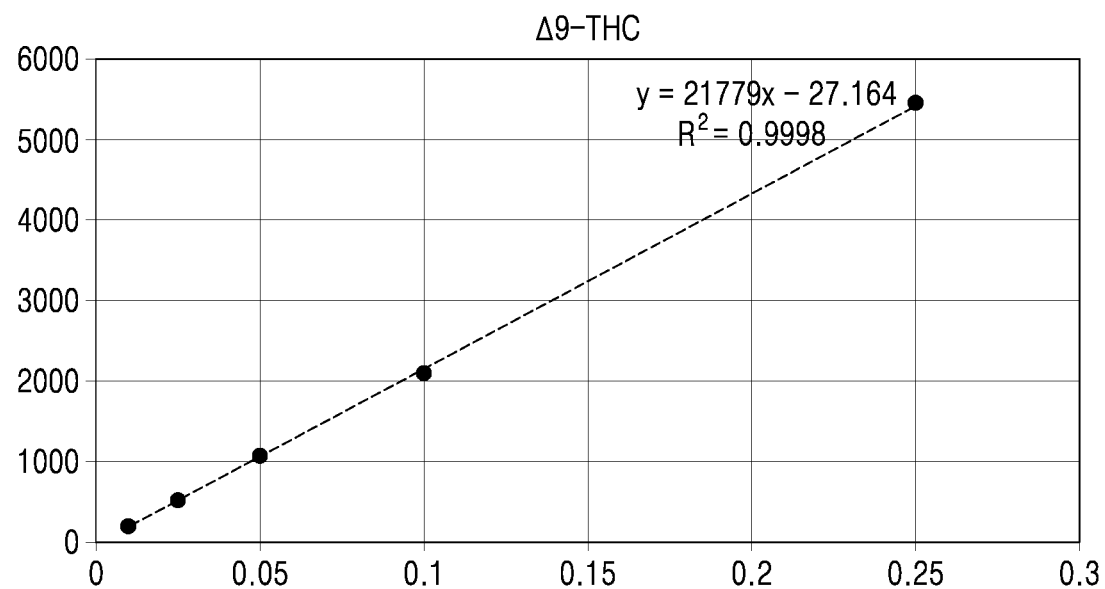
FIG. 3 shows a calibration curve constructed by analyzing Δ9-THC according to concentrations.

FIG. 3 shows a calibration curve constructed by analyzing Δ9-THC according to concentrations.

Figure 4:
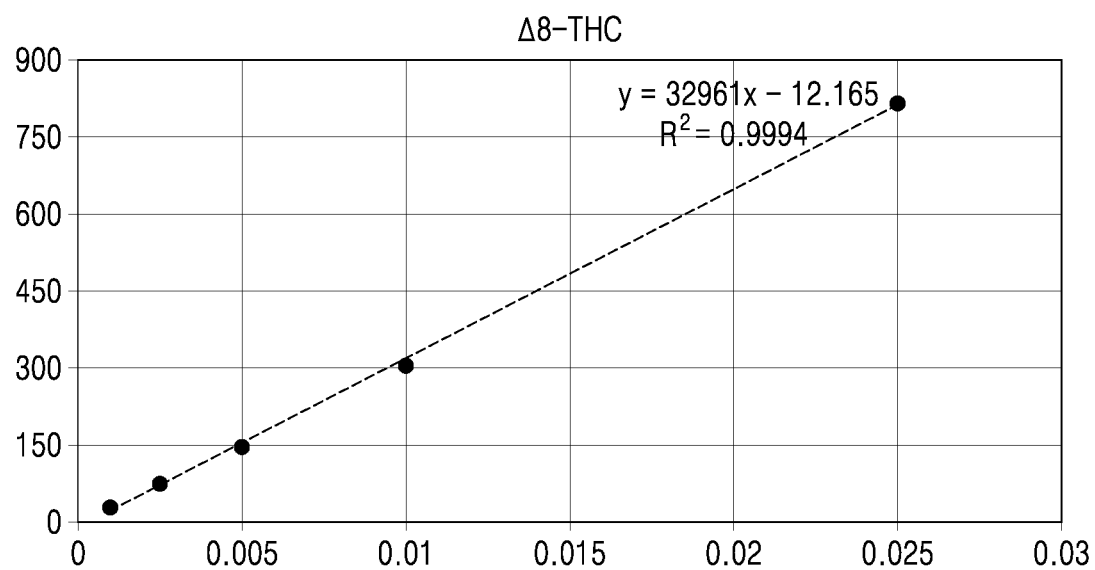
FIG. 4 shows a calibration curve constructed by analyzing Δ8-THC according to concentrations.

FIG. 4 shows a calibration curve constructed by analyzing Δ8-THC according to concentrations.

Figure 5:
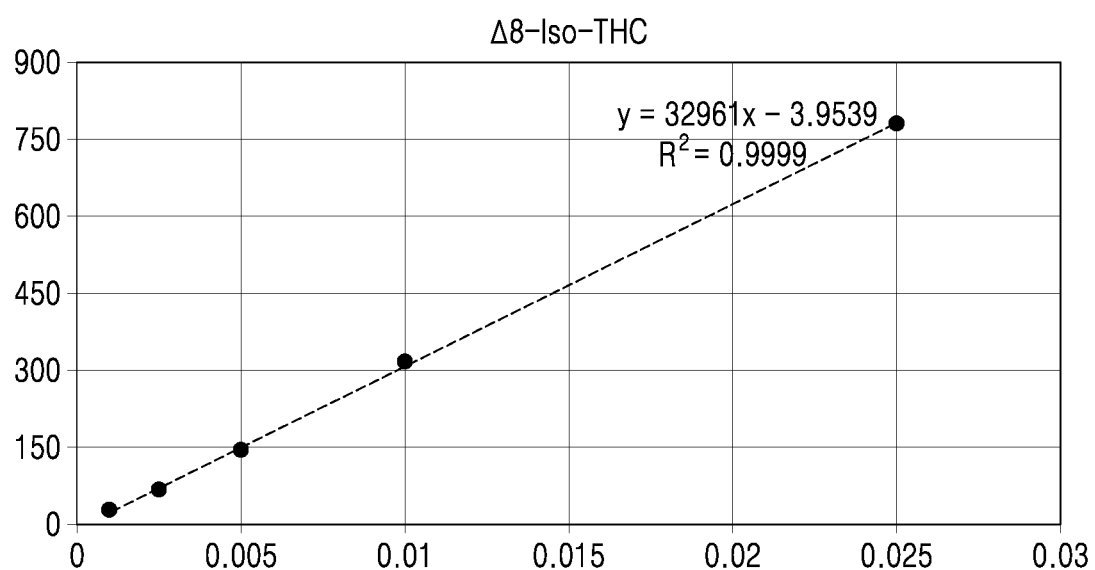
FIG. 5 shows a calibration curve constructed by analyzing Δ8-iso-THC according to concentrations.

FIG. 5 shows a calibration curve constructed by analyzing Δ8-iso-THC according to concentrations.

Figure 6:
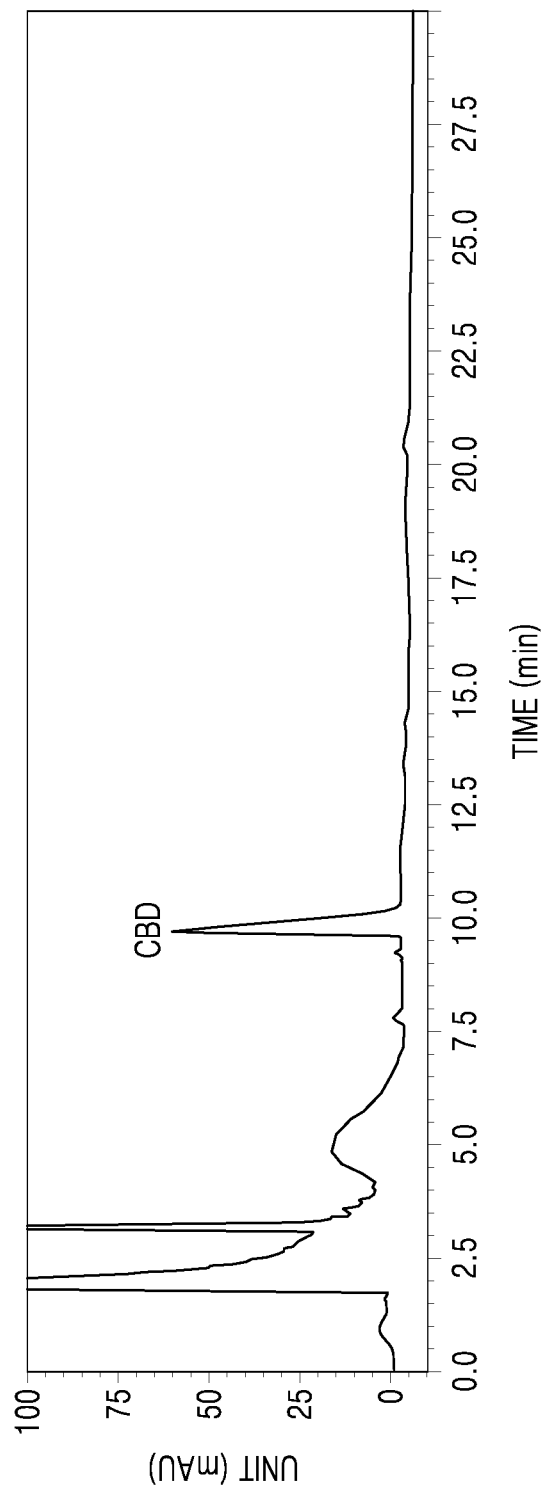
FIG. 6 shows a UPLC chromatogram of analyzing cannabinoid ingredients of Example 2.

FIG. 6 shows a UPLC chromatogram of analyzing cannabinoid ingredients of Example 2.

Figure 7:
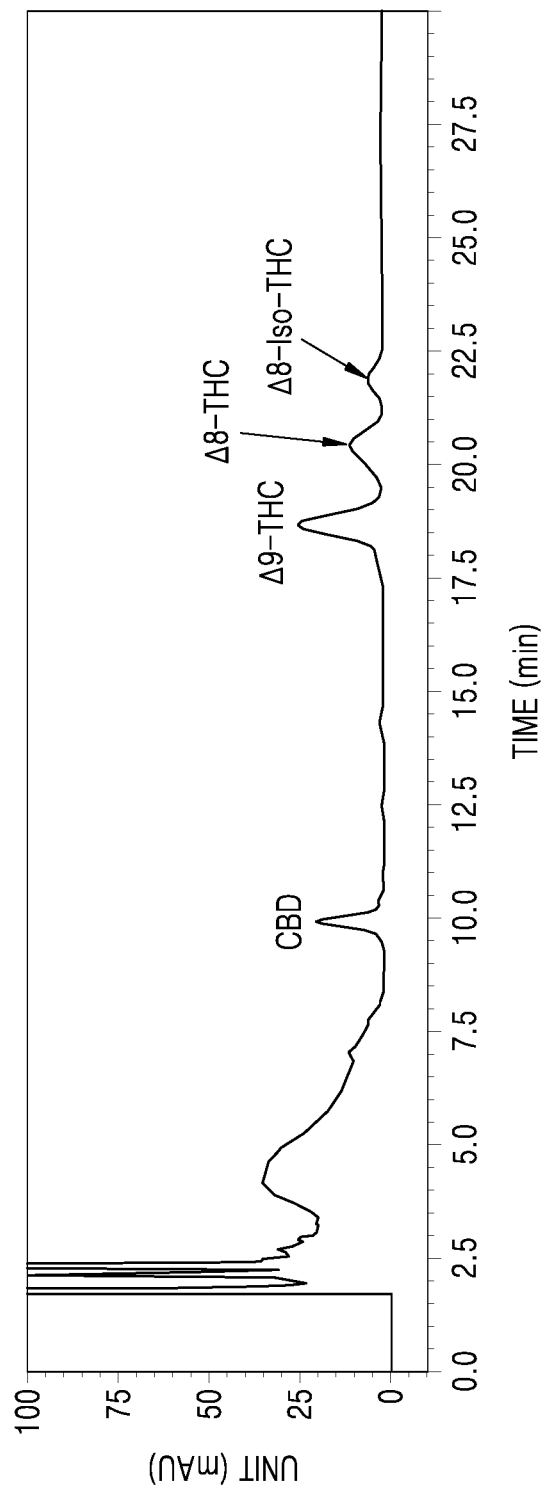
FIG. 7 shows a UPLC chromatogram of analyzing cannabinoid ingredients of Example 28.

FIG. 7 shows a UPLC chromatogram of analyzing cannabinoid ingredients of Example 28.

Figure 8:
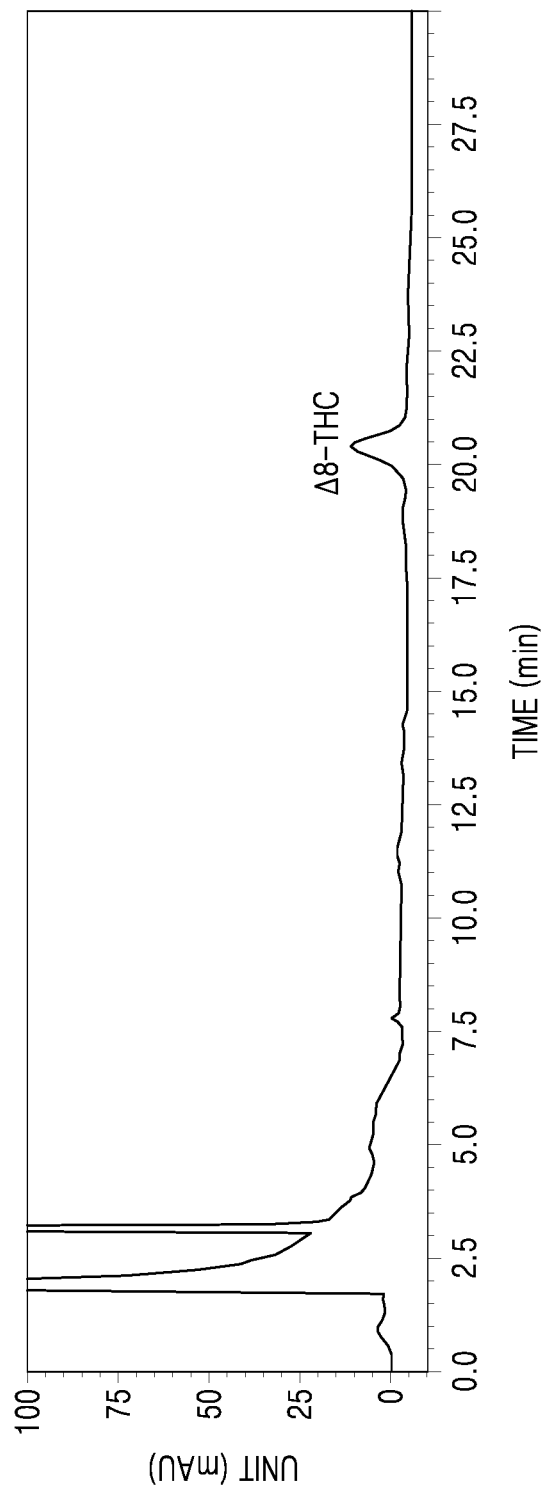
FIG. 8 shows a UPLC chromatogram of analyzing cannabinoid ingredients of Example 64.

FIG. 8 shows a UPLC chromatogram of analyzing cannabinoid ingredients of Example 64.

Figure 9:
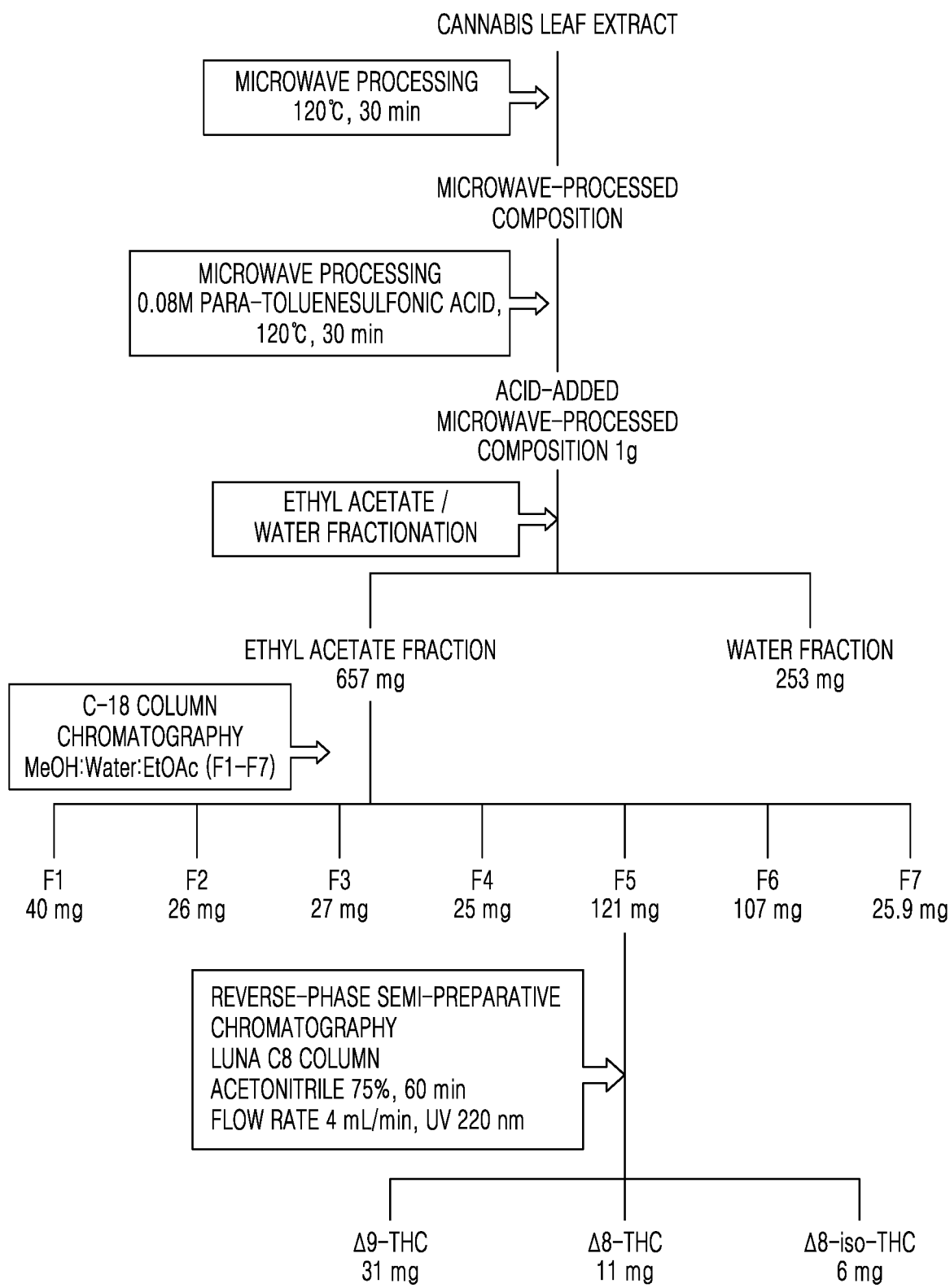
FIG. 9 shows a diagram of a process of isolating Δ9-THC, Δ8-THC, and Δ8-iso-THC from a processed product of Example 28.

FIG. 9 shows a diagram of a process of isolating Δ9-THC, Δ8-THC, and Δ8-iso-THC from the processed product of Example 28.

Figure 10:
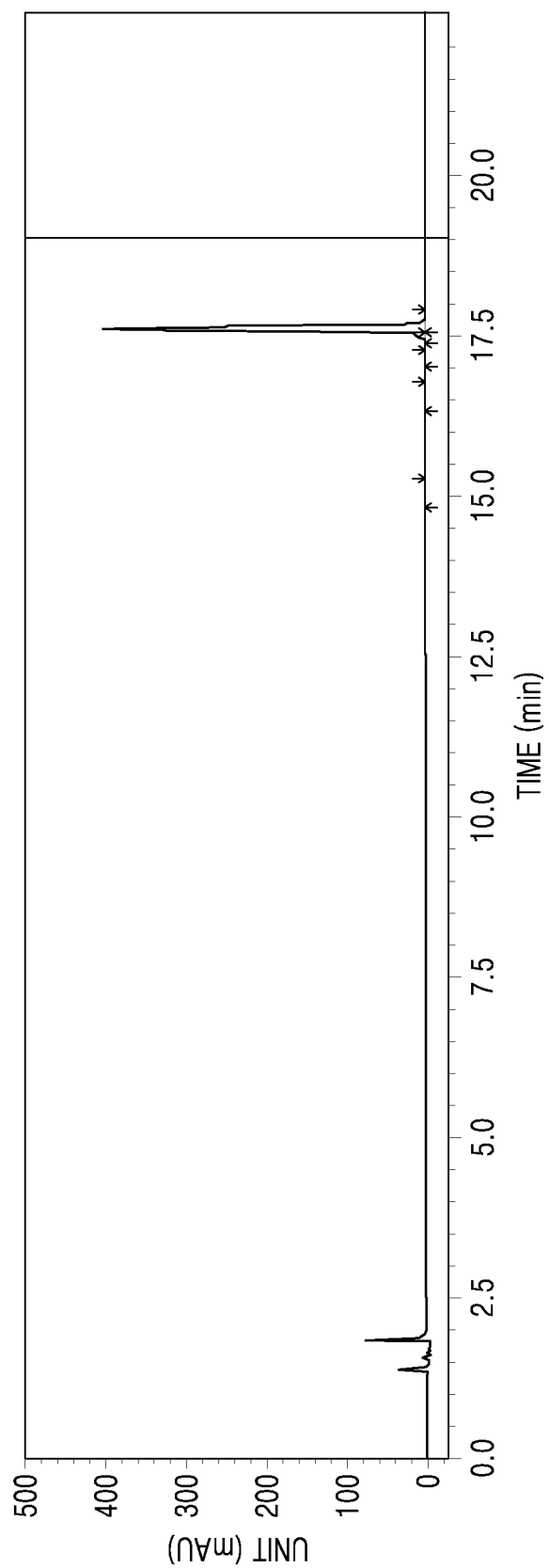
FIG. 10 shows a UPLC chromatogram of analyzing purity of Δ9-THC isolated in Experimental Example 3.

FIG. 10 shows a UPLC chromatogram of analyzing purity of Δ9-THC isolated in Experimental Example 3.

Figure 11:
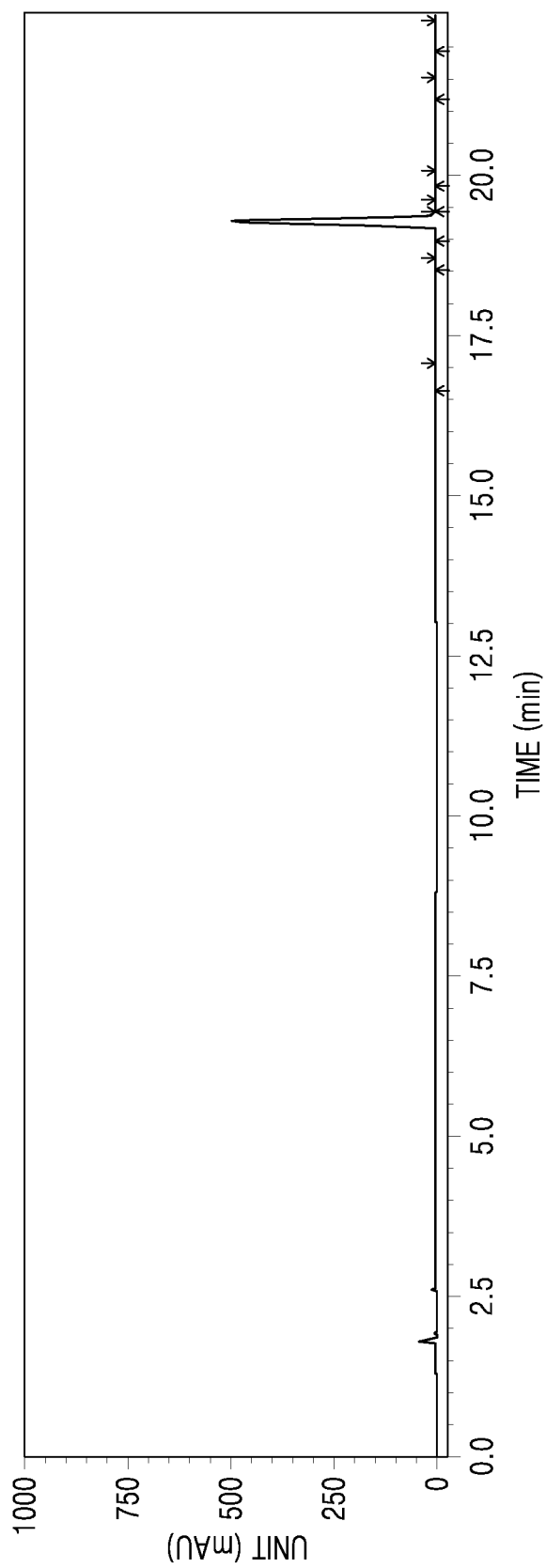
FIG. 11 shows a UPLC chromatogram of analyzing purity of Δ8-THC isolated in Experimental Example 3.

FIG. 11 shows a UPLC chromatogram of analyzing purity of Δ8-THC isolated in Experimental Example 3.

Figure 12:
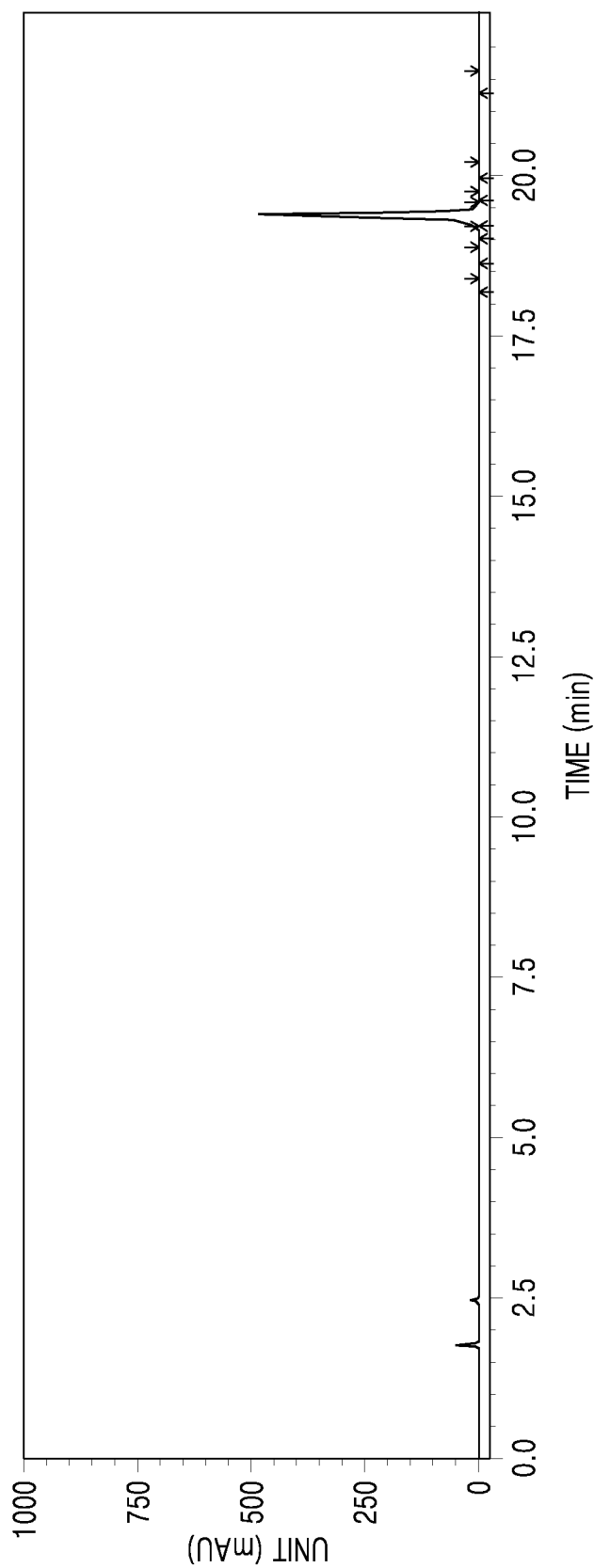
FIG. 12 shows a UPLC chromatogram of analyzing purity of Δ8-iso-THC isolated in Experimental Example 3.

FIG. 12 shows a UPLC chromatogram of analyzing purity of Δ8-iso-THC isolated in Experimental Example 3.

The arrows in FIGS. 10 to 12 indicate integration area for measuring area values of peaks shown in UV chromatogram.

Further, the contents of CBD and Δ9-THC according to kinds of acids are summarized in Table 1.

TABLE 1

| Item | Acid | CBD(mg) | Δ9-THC(mg) | CBD + Δ9-THC(mg) | Δ9-THC production yield* | Δ9-THC content %** |
|---|---|---|---|---|---|---|
| Example 2 | — | 62.0 | — | 62.0 | — | — |
| Example 3 | Acetic acid | 48.1 | 12.7 | 60.8 | 20.5 | 20.9 |
| Example 4 | Citric acid | 44.7 | 11.0 | 55.7 | 17.7 | 19.7 |
| Example 5 | Formic acid | 45.8 | 11.2 | 57.0 | 18.1 | 19.6 |
| Example 6 | Hydrochloric acid | 47.4 | 4.4 | 51.8 | 7.1 | 8.5 |
| Example 7 | Sulfuric acid | 2.1 | 11.7 | 13.8 | 18.9 | 84.8 |
| Example 8 | Nitric acid | — | 5.1 | 5.1 | 8.2 | 100 |
| Example 9 | PTSA | 8.5 | 38.5 | 47.0 | 62.1 | 81.9 |
| Example 10 | MSA | 3.9 | 30.4 | 34.3 | 49.0 | 88.6 |
| Example 11 | CSA | 35.3 | 17.0 | 52.3 | 27.4 | 32.5 |

*Δ9-THC production yield = (Δ9-THC (mg) produced in each Example/62.0 mg (amount of Δ9-THC produced in Example 2, regarded as 100%) × 100
**Δ9-THC content % = {Δ9-THC/(CBD + Δ9-THC)} × 100

In Table 1, the contents of CBD and Δ9-THC are expressed in mg per 1 g of the extract according to each acid, after adding seven kinds of acids, acetic acid (Example 3), citric acid (Example 4), formic acid (Example 5), hydrochloric acid (Example 6), sulfuric acid (Example 7), nitric acid (Example 8), PTSA (Example 9), MSA (Example 10), and CSA (Example 11) at a concentration of 0.08 M to 100 mg of the *cannabis* microwave-processed product, respectively, and carrying out microwave processing at 80° C. for 20 min. When acetic acid, citric acid, formic acid, and hydrochloric acid were added, a small amount (4.4 mg to 12.7 mg) of CBD was converted to Δ9-THC, and most CBD remained. When sulfuric acid and nitric acid were added, CBD was mostly eliminated and thus 0 mg to 2.1 mg thereof remained, but 5.1 mg to 11.7 mg of Δ9-THC was produced. When PTSA was added, 38.5 mg of Δ9-THC was produced and 8.5 mg of CBD remained. When MSA was added, 30.4 mg of Δ9-THC was produced and 3.9 mg of CBD remained. However, this result is not comparable to the result of PTSA. Therefore, it was observed that PTSA is the most effective in converting CBD to THC through cyclization by microwave processing. PTSA, MSA, and CSA were used as examples of sulfonic acid, and other sulfonic acids may also be used. The sulfonic acid may be, for example, the sulfonic acid of Formula I.

Further, Table 2 summarizes the results of calculating the contents of CBD and Δ9-THC in UPLC chromatograms obtained after adding PTSA to the *cannabis* microwave-processed product and carrying out microwave processing using many different solvents.

In Table 2, the contents of CBD and Δ9-THC are expressed in mg per 1 g of the extract, after dissolving 100 mg of the *cannabis* microwave-processed product of Example 2 in different solvents, respectively and adding PTSA to carry out microwave processing. Only CBD was present in an amount of 62.0 mg in the initial *cannabis* extract (Example 1). As microwave irradiation was carried out, a cyclization reaction occurred, leading to conversion of CBD to Δ9-THC. As a result, the content of Δ9-THC in the processed product was increased. The conversion amount of Δ9-THC by microwave processing was 38.5 mg which was the largest amount, when ethyl acetate was used as the solvent, and the amount was decreased in this order of ethanol (32.2 mg), propanol (31.9 mg), butanol (28.1 mg), acetone (25.1 mg), acetonitrile (12.3 mg), hexane (6.5 mg), chloroform (5.1 mg), and dichloromethane (3.9 mg). When microwave processing was carried out by adding an acid in the presence of ethyl acetate, the highest conversion (62.1%) of CBD to Δ9-THC was observed.

Further, Table 3 summarizes the results of calculating the contents of CBD and Δ9-THC in UPLC chromatogram obtained after adding different concentrations of PTSA to the *cannabis* leaf microwave-processed product, and carrying out microwave processing with varying temperature and time.

TABLE 2

| Item | Solvent | CBD | Δ9-THC | CBD + Δ9-THC | Δ9-THC production yield* | Δ9-THC content %** |
|---|---|---|---|---|---|---|
| Example 2 | — | 62.0 mg | — | 62.0 mg | — | — |
| Example 12 | Ethanol | 2.4 mg | 32.2 mg | 34.6 mg | 51.9% | 93.1% |
| Example 13 | Propanol | 2.2 mg | 31.9 mg | 34.1 mg | 51.5% | 93.5% |
| Example 14 | Butanol | 3.1 mg | 28.1 mg | 31.2 mg | 45.3% | 90.1% |
| Example 15 | Acetonitrile | 6.2 mg | 12.3 mg | 18.5 mg | 29.8% | 66.5% |
| Example 16 | Ethyl acetate | 8.5 mg | 38.5 mg | 47.0 mg | 62.1% | 81.9% |
| Example 17 | Acetone | 4.2 mg | 25.1 mg | 29.3 mg | 40.5% | 85.7% |
| Example 18 | 2-Butanone | 5.1 mg | 21.7 mg | 26.8 mg | 35.0% | 81.0% |
| Example 19 | Chloroform | 2.7 mg | 5.1 mg | 7.8 mg | 8.2% | 65.4% |
| Example 20 | Dichloromethane | 3.4 mg | 3.9 mg | 7.3 mg | 6.3% | 53.4% |
| Example 21 | Hexane | 3.0 mg | 6.5 mg | 9.5 mg | 10.5% | 68.4% |

*Δ9-THC production yield and Δ9-THC content % are the same as defined in Table 1.

TABLE 3

| Item | Acid concentration (M) | Temperature(° C.)-Time(min) | CBD | Δ9-THC | CBD + Δ9-THC | Δ9-THC production yield* | Δ9-THC content %** |
|---|---|---|---|---|---|---|---|
| Example 2 | | | 62.0 mg | — | 62.0 mg | — | — |
| Example 22 | 0.004 | 80-30 | 53.3 mg | 1.2 mg | 54.5 mg | 1.9% | 2.2% |
| Example 23 | 0.02 | 80-30 | 40.3 mg | 8.5 mg | 48.8 mg | 13.7% | 17.4% |
| Example 24 | 0.04 | 80-30 | 36.2 mg | 14.0 mg | 50.2 mg | 22.6% | 27.9% |
| Example 25 | | 80-60 | 10.8 mg | 21.6 mg | 32.4 mg | 34.8% | 66.7% |
| Example 26 | | 80-90 | 3.1 mg | 18.8 mg | 21.9 mg | 30.3% | 85.8% |
| Example 27 | 0.08 | 80-10 | 22.9 mg | 28.3 mg | 51.2 mg | 45.6% | 55.3% |
| Example 28 | | 80-20 | 8.5 mg | 38.5 mg | 47.0 mg | 62.1% | 81.9% |
| Example 29 | | 80-30 | 2.4 mg | 24.4 mg | 26.8 mg | 39.4% | 91.0% |
| Example 30 | | 80-40 | — | 18.7 mg | 18.7 mg | 30.2% | 100% |
| Example 31 | 0.12 | 80-10 | 12.6 mg | 21.3 mg | 33.9 mg | 34.4% | 62.8% |
| Example 32 | | 80-20 | 1.3 mg | 20.6 mg | 21.9 mg | 33.2% | 94.1% |
| Example 33 | | 80-30 | — | 14.3 mg | 14.3 mg | 23.1% | 100% |
| Example 34 | 0.08 | 50-30 | 52.1 mg | 3.4 mg | 55.5 mg | 5.5% | 6.1% |
| Example 35 | | 50-60 | 47.6 mg | 4.8 mg | 52.4 mg | 7.7% | 9.2% |
| Example 36 | | 50-90 | 42.3 mg | 6.1 mg | 48.4 mg | 9.8% | 12.6% |
| Example 37 | | 90-10 | 5.3 mg | 27.6 mg | 32.9 mg | 44.5% | 83.9% |
| Example 38 | | 90-20 | 1.2 mg | 21.4 mg | 22.6 mg | 34.5% | 94.7% |
| Example 39 | | 90-30 | — | 13.8 mg | 13.8 mg | 22.3% | 100 |

*Δ9-THC production yield and Δ9-THC content % are the same as defined in Table 1.

In Table 3, the contents of CBD and Δ9-THC are expressed in mg per 1 g of the extract, after adding different concentrations of PTSA to the *cannabis* leaf microwave-processed product of Example 2 and carrying out microwave processing under various temperature and time conditions. When microwave processing was carried out by adding a small amount of PTSA, conversion of CBD to Δ9-THC did not occur at 0.004 M, 0.02 M, and 0.04 M, whereas the reaction rapidly occurred at 0.08 M. In Example 28, the conversion amount of Δ9-THC was 38.5 mg, which was the highest. At 0.12 M, the conversion amount of Δ9-THC was up to 21.3 mg, indicating that the excessive addition rather eliminated the conversion. The concentration of PTSA was fixed at 0.08 M, and microwave processing was carried out at 50° C. As a result, although the processing was carried out for 90 min or more, conversion to Δ9-THC did not occur, and at 90° C., Δ9-THC was produced up to 27.6 mg, which did not reach the production amount of the reaction at 80° C. PTSA was added, and microwave processing was carried out under various conditions. As a result, when processing was carried out at 0.08 M and 80° C. for 20 min, Δ9-THC was produced up to 38.5 mg.

Further, Table 4 summarizes the results of calculating the contents of CBDA, CBD, and Δ9-THC in UPLC chromatogram of the processed product obtained after adding an ethyl acetate solvent and para-toluenesulfonic acid of 0.08 M to the *cannabis* leaf extract obtained in Example 1, and carrying out microwave irradiation at 80° C. with varying time.

TABLE 4

| Item | Temperature(° C.)-Time(min) | CBDA | CBD | Δ9-THC | CBDA + CBD + Δ9-THC | Δ9-THC production yield* | Δ9-THC content %** |
|---|---|---|---|---|---|---|---|
| Example 1 | — | 68.2 mg | 8.9 mg | — | 77.1 mg | | |
| Example 40 | 80-10 | 24.2 mg | 2.2 mg | 13.9 mg | 40.3 mg | 20.4% | 34.5% |
| Example 41 | 80-20 | 14.3 mg | 2.0 mg | 19.1 mg | 35.4 mg | 28.0% | 54.0% |
| Example 42 | 80-30 | 5.8 mg | 0.4 mg | 15.2 mg | 21.4 mg | 22.2% | 71.0% |
| Example 43 | 80-40 | 2.6 mg | 0 mg | 14.4 mg | 17.0 mg | 21.1% | 84.7% |
| Example 44 | 80-50 | 0 mg | 0 mg | 10.0 mg | 10.0 mg | 14.7% | 100 |

*Δ9-THC production yield = (Δ9-THC (mg) produced in each Example/62.0 mg (amount of Δ9-THC produced in Example 2, regarded as 100%) × 100

**Δ9-THC content % = {Δ9-THC/(CBD + Δ9-THC)} × 100

In Table 4, the contents of CBDA, CBD, and Δ9-THC are expressed in mg per 1 g of the extract, after adding an ethyl acetate solvent and para-toluenesulfonic acid to the *cannabis* leaf extract of Example 1 and carrying out microwave irradiation at 80° C. for 10 min to 50 min. The amount of produced Δ9-THC was 13.9 mg, 19.1 mg, 15.2 mg, 14.4 mg, and 10.0 mg, when the processing was carried out for 10 min, 20 min, 30 min, 40 min, and 50 min, respectively. The maximum conversion was observed when the processing was carried out for 20 min, and thereafter, the conversion was gradually reduced.

Further, Table 5 summarizes the results of calculating the contents of CBD and Δ9-THC in UPLC chromatogram obtained after adding PTSA to the *cannabis* microwave-processed product and carrying out processing in an oil bath.

of the *cannabis* extract. The conversion amount of Δ9-THC was increased as the processing temperature and time were increased. When processing was carried out by using ethyl acetate at 80° C. for 30 min, Δ9-THC was produced up to 3.7 mg. When processing was carried out by using ethanol as a solvent at 80° C. for 40 min, Δ9-THC was produced up to 3.3 mg. When processing was carried out by using propanol as a solvent at 80° C. for 40 min, Δ9-THC was produced up to 3.7 mg. When microwave processing of *cannabis* was carried out by adding an acid in the presence of many different organic solvents, conversion of CBD to Δ9-THC by a cyclization reaction was also observed, as in the microwave processing of the *cannabis* extract.

The above experimental results showed that when microwave processing of the *cannabis* extract and *cannabis* was

TABLE 5

| Item | Acid concentration (M) | Temperature(° C.)-Time(min) | CBD | Δ9-THC | CBD + Δ9-THC | Δ9-THC production yield* | Δ9-THC content %** |
|---|---|---|---|---|---|---|---|
| Example 2 | — | — | 62.0 mg | 0.0 | 62.0 mg | — | — |
| Example 45 | 0.08 | 80-30 | 53.3 mg | 4.6 mg | 57.9 mg | 7.4% | 7.9% |
| Example 46 | | 80-60 | 47.2 mg | 7.9 mg | 55.1 mg | 12.7% | 14.3% |
| Example 47 | | 80-90 | 40.2 mg | 11.9 mg | 52.1 mg | 19.2% | 22.8% |
| Example 48 | | 80-120 | 34.8 mg | 15.8 mg | 50.6 mg | 25.5% | 31.2% |
| Example 49 | | 80-180 | 19.4 mg | 19.3 mg | 38.7 mg | 31.1% | 49.9% |
| Example 50 | | 80-240 | 7.6 mg | 18.6 mg | 26.2 mg | 30.0% | 71.0% |
| Example 51 | | 80-360 | 1.3 mg | 16.2 mg | 17.5 mg | 26.1% | 92.6% |

*Δ9-THC production yield and Δ9-THC content % are the same as defined in Table 1.

In Table 5, the contents of CBD and Δ9-THC are expressed in mg per 1 g of the extract, after adding PTSA to the *cannabis* extract microwave-processed product of Example 2 and carrying out processing at 80° C. in the oil bath. When processing was carried out in the oil bath for 3 hr, the maximum Δ9-THC conversion (19.3 mg) was observed (Example 49), which was a lower conversion rate and required a longer processing time, as compared with microwave processing.

Further, Table 6 summarizes the results of calculating the contents of CBD and Δ9-THC in UPLC chromatogram of the processed product after carrying out microwave processing with varying temperature and time by directly using *cannabis* leaves in an ethyl acetate solvent.

carried out by using many different organic solvents in addition to ethanol, a cannabinoid component CBD was more efficiently converted to Δ9-THC.

For example, a microwave-processed product having the Δ9-THC content of 20% to 100%, for example, 25% to 100%, 30% to 100%, 35% to 100%, 40% to 100%, 45% to 100%, or 50% to 100%, based on the weight of the major cannabinoid components of *cannabis*, may be obtained.

Experimental Example 2: Analysis for Identification of Δ9-THC, Δ8-THC, and Δ8-iso-THC (1) Experimental Method Based on values of Δ9-THC, Δ8-THC, and Δ8-iso-THC calibration curves, cannabinoids in the *cannabis* extracts and

TABLE 6

| Item | Solvent | Temperature(° C.)-Time(min) | CBD | Δ9-THC | CBD + Δ9-THC | Δ9-THC production yield* | Δ9-THC content %** |
|---|---|---|---|---|---|---|---|
| Example 52 | | | 5.9 mg | | 5.9 mg | | |
| Example 53 | ethyl acetate | 80-20 | 2.0 mg | 2.4 mg | 4.4 mg | 40.7% | 54.5% |
| Example 54 | | 80-30 | 0.8 mg | 3.7 mg | 4.5 mg | 62.7% | 82.2% |
| Example 55 | | 80-40 | 0.3 mg | 2.1 mg | 2.4 mg | 35.6% | 87.5% |
| Example 56 | Ethanol | 80-20 | 2.7 mg | 1.7 mg | 4.4 mg | 28.8% | 38.6% |
| Example 57 | | 80-30 | 1.7 mg | 2.6 mg | 4.3 mg | 44.1% | 60.5% |
| Example 58 | | 80-40 | 0.7 mg | 3.3 mg | 4.0 mg | 55.9% | 82.5% |
| Example 59 | | 80-50 | 0.3 mg | 2.0 mg | 2.3 mg | 33.9% | 87.0% |
| Example 60 | propanol | 80-20 | 2.4 mg | 1.9 mg | 4.3 mg | 32.2% | 44.2% |
| Example 61 | | 80-30 | 1.5 mg | 2.2 mg | 3.7 mg | 37.3% | 59.5% |
| Example 62 | | 80-40 | 0.6 mg | 3.1 mg | 3.7 mg | 52.5% | 83.8% |
| Example 63 | | 80-50 | 0.4 mg | 1.8 mg | 2.2 mg | 30.5% | 81.8% |

*Δ9-THC production yield and Δ9-THC content % are the same as defined in Table 1.

In Table 6, the contents of CBD and Δ9-THC are expressed in mg per 1 g of *cannabis*, after adding PTSA to the *cannabis* leaves and carrying out microwave processing in various solvents. As a result of microwave-processing of *cannabis*, conversion of CBD to Δ9-THC by a cyclization reaction was also observed, as in the microwave-processing the processed extracts obtained in Examples were analyzed, and repeated in triplicate to confirm reproducibility. As for Δ9-THC, Δ8-THC, and Δ8-iso-THC single ingredients used in the experiments, purity of 96.8% (Δ9-THC), purity of 95.3% (Δ8-THC), and purity of 96.0% (Δ8-iso-THC) directly isolated from the microwave processed product of the *cannabis* leaf extract were used. According to the general calibration curve analysis method, Δ9-THC, Δ8-THC, and Δ8-iso-THC were prepared at 10 ppm, 25 ppm, 50 ppm, 100 ppm, and 250 ppm, respectively, and calibration curves were constructed. An elution solvent A and an elution solvent B used in ultra-performance liquid chromatography (UPLC) were water and acetonitrile, respectively, and each was pumped using two pumps. 3 μl of the standard aqueous solution was injected into a reverse-phase column for analysis (Phenomenex Luna Omega 1.6μ Polar C18, 150 mm×2.1 mm) using a syringe, and an elution solvent consisting of 25% by volume of A and 75% by volume of B was applied at a flow rate of 1.0 mL/min for 30 min. After the above procedures, each ingredient isolated from the column was analyzed by UV spectrum.

(2) Experimental Results

As a result of the experiments, each ingredient isolated from the column was analyzed by UPLC analysis of the *cannabis* extracts, and results of FIGS. 6 to 8 were obtained by the analysis of UPLC chromatograms.

Further, Table 7 summarizes the results of calculating the contents of Δ9-THC, Δ8-THC, and Δ8-iso-THC in UPLC chromatograms obtained after adding para-toluenesulfonic acid to the *cannabis* microwave-processed product and carrying out microwave processing using ethyl acetate and benzene.

acetone, 2-butanone, chloroform, dichloromethane, hexane, a mixture thereof, or a mixture of one or more of the solvents and water.

Experimental Example 3: Isolation of Cannabinoid from Microwave Processed Product of *Cannabis* Leaf Extract (1) Experimental Method The microwave-processed product of *cannabis*, which was obtained in Example 28, was applied to reverse-phase column chromatography to separate seven fractions, including a fraction having a high concentration of Δ9-THC, Δ8-THC, and Δ8-iso-THC.

1 g of the processed product of Example 28 was adsorbed onto 2 g of C18 (Nacalai tesque, Cosmosil C18), and then a glass column having an internal diameter of 2.8 cm was packed with C18 up to 10.0 cm in height, and a mixed solvent of methanol and water, and ethyl acetate were applied thereto. The elution solvents were 50%, 60%, 70%, 80%, 90%, and 100% methanol and 100% ethyl acetate, and thus a total of seven fractions of F1 to F7 were obtained.

The seven fractions thus separated were analyzed by the method of Experimental Example 1.

Δ9-THC, Δ8-THC, and Δ8-iso-THC were analyzed in the obtained F5 fraction to attempt isolation thereof. Reverse-

TABLE 7

| Item | Solvent | CBD | Δ9-THC | Δ8-THC | Δ8-iso-THC | CBD + Δ9-THC + Δ8-THC + Δ8-iso-THC | Weight ratio of Δ9-THC to Δ8-THC* | Content % ** of Δ9-THC to Δ8-THC |
|---|---|---|---|---|---|---|---|---|
| Example 64 | Benzene | — | — | 17.2 mg | — | 17.2 mg | — | — |
| Example 28 | Ethyl acetate | 8.1 mg | 38.2 mg | 11.0 mg | 4.2 mg | 61.5 mg | 1.0:3.5 | 347.3% |
| Example 29 | Ethyl acetate | 2.4 mg | 24.4 mg | 13.2 mg | 5.3 mg | 45.3 mg | 1.0:1.8 | 184.8% |
| Example 30 | Ethyl acetate | — | 18.7 mg | 11.9 mg | 4.2 mg | 34.8 mg | 1.0:1.6 | 157.1% |

*Weight ratio of Δ9-THC to Δ8-THC = Δ8-THC mg: Δ9-THC mg
** content % of Δ9-THC to Δ8-THC = (Δ9-THC/Δ8-THC) × 100

In Table 7, the contents of CBD, Δ9-THC, Δ8-THC, and Δ8-iso-THC are expressed in mg per 1 g of the *cannabis*, after adding para-toluenesulfonic acid to the *cannabis* leaf extract and carrying out microwave processing using benzene as a solvent, and the contents were compared with those of Example 28. As a result of analyzing Example 28 by the method of Experimental Example 2, the contents of Δ9-THC, Δ8-THC, and Δ8-iso-THC were 38.2 mg, 11.0 mg, and 4.2 mg, respectively and a ratio thereof was 9.1:2.6:1, indicating that Δ9-THC was produced with high selectivity. However, in the presence of the benzene solvent, 17.2 mg of Δ8-THC was only produced, and Δ9-THC and Δ8-iso-THC were not produced. These results indicate that the microwave processing by adding para-toluenesulfonic acid in the presence of the ethyl acetate solvent exhibits high selectivity for Δ9-THC production, as compared with the known method.

Ethyl acetate was used only for illustrating, and the solvent may be a protonic polar solvent or an aprotonic polar or non-polar solvent, except for benzene. The solvent may be C1-C6 alcohol, C3-C10 ester, for example, C3-C10 acetate, C3-C10 ketone, C1-C6 unsubstituted or halogenated hydrocarbon, C2-C10 cyclic ether, a mixture thereof, or a mixture of one or more of the solvents and water. The solvent may be ethanol, propanol, acetonitrile, ethyl acetate, phase semi-preparative chromatography (stationary phase: Luna C8(2) column, Phenomenex, particle size of 5 μm, length of 250 mm×10 mm) was used to carry out isolation while developing an eluent with initial acetonitrile:water=75:25 (v/v) for 60 min to 90 min at a flow rate of 4 mL/min, and three major peak at UV 220 nm were obtained.

(2) Experimental Results

As a result of the experiment, Example 28 was separated into seven fractions by reverse-phase C18 column chromatography. The fractions were 40 mg (fraction F1), 26 mg (fraction F2), 27 mg (fraction F3), 25 mg (fraction F4), 121 mg (fraction F5), 107 mg (fraction F6), and 259 mg (fraction F7), respectively. Δ9-THC, Δ8-THC, and Δ8-iso-THC were not observed in the fractions F1 to F4 and F6, F7, whereas large amounts of Δ9-THC, Δ8-THC, and Δ8-iso-THC were observed in the fraction F5, which was then separated by reverse-phase semi-preparative chromatography. As a result, 31 mg, 11 mg, and 6 mg were obtained, respectively.

In conclusion, when Δ9-THC, Δ8-THC, and Δ8-iso-THC were isolated from the microwave-processed product of the *cannabis* extract by reverse-phase C18 column chromatography and reverse-phase semi-preparative chromatography, Δ9-THC among the three compounds was produced in a larger amount than the other two compounds, indicating that Δ9-THC is a major component. In detail, the present inventors developed a method of producing 31 mg (96.8%) of Δ9-THC, 11 mg (95.3%) of Δ8-THC, and 6 mg (96.0%) of Δ8-iso-THC from 1 g of the *cannabis* microwave composition by adding an acid thereto and inducing the cyclization reaction of CBD through microwave irradiation.

According to a method of isolating Δ9-THC from a *cannabis* plant according to an aspect, Δ9-THC may be efficiently isolated from the *cannabis* plant. According to the method of isolating Δ9-THC from the *cannabis* plant according to an aspect, Δ9-THC may be efficiently isolated from the *cannabis* plant with high selectivity, as compared with Δ8-THC.

A composition including THC isolated by the above method according to another aspect has a high content of THC.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A method of isolating Δ9-tetrahydrocannabinol (THC) from a *cannabis* plant, the method comprising:
   irradiating microwaves to a reaction mixture comprising a cannabidiol (CBD)-comprising sample, a Lewis acid, and a solvent in an airtight container;
   wherein the microwave irradiation is carried out at 50° C. to 100° C., 1 atm to 15 atm, and for 10 min to 90 min;
   wherein the solvent is ethyl acetate or a mixture of ethyl acetate and water; and
   wherein the Lewis acid is para-toluenesulfonic acid, methanesulfonic acid, or camphor-10-sulfonic acid.

2. The method of claim 1, wherein a concentration of the Lewis acid is 0.004 M to 0.12 M.

3. The method of claim 1, wherein the CBD-comprising sample is obtained by a method including irradiating microwaves to a mixture comprising *cannabis* leaves or a solvent extract thereof and a solvent in an airtight container, or the solvent extract is obtained by a method including incubating a reaction mixture comprising *cannabis* leaves and a solvent.

4. The method of claim 1, wherein a product obtained by the microwave irradiation has higher selectivity for Δ9-THC than Δ8-THC or iso-THC.

5. The method of claim 1, further comprising isolating Δ9-THC from the reaction product obtained by the microwave irradiation.

6. The method of claim 3, wherein the solvent for obtaining the CBD-comprising sample is C1-C6 alcohol, C3-C10 ester, C3-C10 ketone, C1-C6 unsubstituted or halogenated hydrocarbon, C2-C10 cyclic ether, a mixture thereof, or a mixture of one or more of the solvents and water.

7. The method of claim 3, wherein the microwave irradiation for obtaining the CBD-comprising sample is carried out at 80° C. to 150° C.

8. The method of claim 3, wherein the microwave irradiation for obtaining the CBD-comprising sample is carried out at 1 atm to 100 atm.

9. The method of claim 3, wherein the microwave irradiation for obtaining the CBD-comprising sample is carried out for 5 min to 180 min.

10. The method of claim 3, wherein the solvent for obtaining the CBD-comprising sample is ethyl acetate.

11. The method of claim 3, wherein, in the product obtained by the microwave irradiation, a ratio of Δ8-THC:Δ9-THC is 1.0:1.6 to 3.5, based on the weight.

* * * * *